United States Patent [19]

Darsow

[11] Patent Number: 5,644,044
[45] Date of Patent: *Jul. 1, 1997

[54] PROCESS FOR THE PREPARATION OF α-D-GLUCOPYRANOSIDO-1,6-MANNITOL AND -SORBITOL FROM α-D-GLUCOPYRANOSIDO-1, 6-FRUCTOSE

[75] Inventor: Gerhard Darsow, Krefeld, Germany

[73] Assignee: Bayer Aktiengesellschaft, Leverkusen, Germany

[*] Notice: The portion of the term of this patent subsequent to May 1, 2015, has been disclaimed.

[21] Appl. No.: 430,996

[22] Filed: Apr. 28, 1995

[30] Foreign Application Priority Data

May 6, 1994 [DE] Germany ............... 44 16 115.8

[51] Int. Cl.[6] .................. C07C 29/132; C07C 31/18
[52] U.S. Cl. .............. 536/18.5; 536/1.11; 536/4.1; 536/124; 568/863
[58] Field of Search ................... 536/1.11, 4.1, 536/18.5, 123.13, 124; 423/53, 61; 568/861, 862, 863

[56] References Cited

U.S. PATENT DOCUMENTS

| | | | |
|---|---|---|---|
| 3,741,776 | 6/1973 | Mitsuhashi et al. | 99/141 |
| 3,865,957 | 2/1975 | Schieweck et al. | 426/213 |
| 4,117,173 | 9/1978 | Schiweck et al. | 426/548 |
| 4,322,569 | 3/1982 | Chao et al. | 568/863 |
| 4,433,184 | 2/1984 | Huibers et al. | 568/863 |
| 4,608,446 | 8/1986 | Möhring et al. | 568/863 |
| 4,684,720 | 8/1987 | Darsow et al. | 536/124 |
| 5,162,517 | 11/1992 | Darsow | 536/124 |

FOREIGN PATENT DOCUMENTS

| | | |
|---|---|---|
| 0039981 | 8/1983 | European Pat. Off. |
| 3403973 | 8/1985 | Germany . |
| 04103546 | 4/1992 | Japan . |
| 639847 | 4/1979 | U.S.S.R. . |

OTHER PUBLICATIONS

Ivchenko et al., *Uzb. Khim. Zh.*, vol. 3 : 66–68, (1990) Abstract provided w/sister application 08/431,603.
Kirgizbaev et al., *Uzb. Khim. Zh.*, vol. 5 : 59–62, (1988) Abstract provided w/sister application 08/431,603.
Pintauro et al., Aiche Symp. Ser. 83(254, Electrochem. Eng.) pp. 34–39, (1987) Abstract provided w/sister application 08/431,603.

*Primary Examiner*—John Kight
*Assistant Examiner*—Howard C. Lee
*Attorney, Agent, or Firm*—Sprung Horn Kramer & Woods

[57] ABSTRACT

Sugar alcohols can be prepared from the corresponding sugars by catalytic hydrogenation in aqueous solution with hydrogen, the hydrogenation being carried out continuously at a hydrogen pressure of 100 to 400 bar and a reaction temperature of 40° to 80° C. on support-free shaped bodies which are arranged in a fixed bed and are composed of pressed powders of alloys of the elements of the iron sub group of sub group VIII of the Periodic Table of the Elements containing elements of sub group VI. The shaped bodies have a compressive strength of 20 to 250 N and an internal surface area of 10 to 80 $m^2/g$.

12 Claims, No Drawings

PROCESS FOR THE PREPARATION OF α-D-GLUCOPYRANOSIDO-1,6-MANNITOL AND -SORBITOL FROM α-D-GLUCOPYRANOSIDO-1, 6-FRUCTOSE

The invention relates to an inexpensive process for the continuous catalytic hydrogenation of α-D-glucopyranosido-1,6-fructose with hydrogen to give a mixture of the diastereomeric sugar alcohols α-D-glucopyranosido-1,6-mannitol and α-D-glucopyranosido-1, 6-sorbitol.

The course of the reaction can be illustrated by the following reaction diagram:

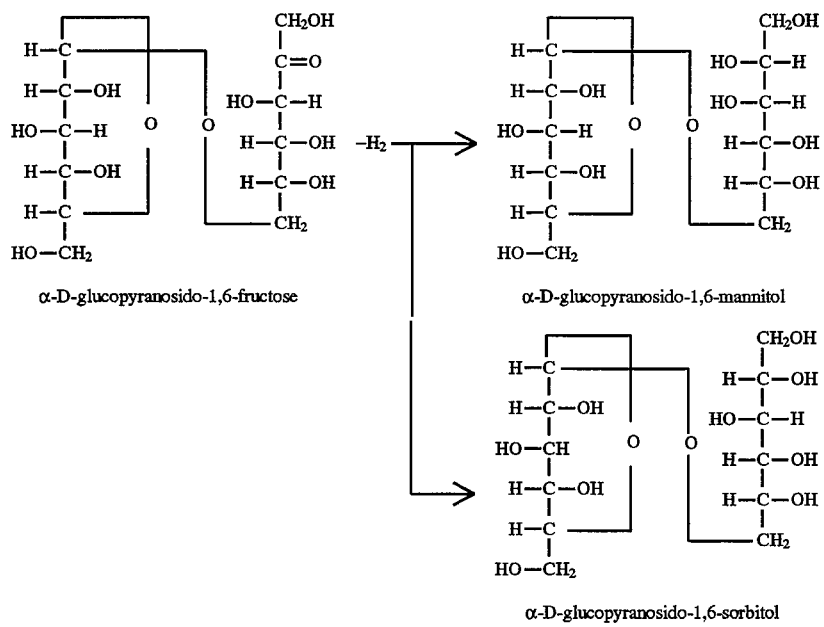

α-D-glucopyranosido-1,6-fructose

α-D-glucopyranosido-1,6-mannitol

α-D-glucopyranosido-1,6-sorbitol

In the known processes for producing α-D-glucopyranosido-1,6-sorbitol (German Patent Specification 2 217 628) and α-D-glucopyranosido-1,6-mannitol (German Auslegeschrift 2 520 173) a pulverulent nickel catalyst is used in each case as hydrogenation catalyst in the discontinuous suspension process (batch process). Discontinuous processes have the disadvantage that their capacity relative to the reaction volume is very small and there is thus a requirement for large reaction apparatuses and storage tanks. Energy consumption and labor requirements are relatively high. Continuous powder catalyst processes which employ a plurality of hydrogenation reactors connected together in a cascade avoids some of these disadvantages. However, there is still the requirement for specifically doping the pulverulent catalyst, pumping it in circulation and quantitatively filtering it off from the reaction product. The catalyst slurry pumps are subject to high mechanical wear. The quantitative removal of the pulverulent catalyst from the reaction product is complex. In addition, there is the high risk of relatively rapidly decreasing the catalyst activity as a result of the additional operations. It is therefore advantageous to allow the reaction to proceed over a fixed catalyst. Such a catalyst must have a high activity which must not decrease over a relatively long period because frequent catalyst changes in fixed-bed reactions are likewise complex.

EP-A 152 779 discloses a process for the continuous hydrogenation of sugars to give the corresponding sugar alcohols on support-free shaped bodies of elements of sub group 8 of the Periodic Table of the Elements, these support-free shaped bodies preferably having been produced by pressing and/or gluing together metal powder. The process gives the desired products in excellent purity in very good yields. However, it would be desirable to reduce the high catalyst costs. Moreover, the aim is always to carry out a process at the lowest possible temperature in order to reduce the energy costs.

It has now been surprisingly been found that metal powders of nickel, cobalt and iron or alloys thereof, which metal powders contain elements of sub group VI of the Periodic Table of the Elements, after being pressed to give shaped bodies not only catalyse equally well the hydrogenation of α-D-glucopyranosido-1,6-fructose to give a mixture of α-D-glucopyranosido-1,6-mannitol and α-D-glucopyranosido-1, 6-sorbitol, but that catalysts made of these metals or metal alloys which are cheaper by 30 to 45% even have a considerably higher hydrogenation activity, so that the hydrogenation reaction can be carried out at a reaction temperature lower by up to 30° C. The powders used in this case can additionally contain certain portions (maximum permissible 10% by weight) of other non-catalytically active metals (e.g. manganese, silicon, aluminum, titanium) without the high activity being decreased.

The invention therefore relates to a process for the preparation of mixtures of α-D-glucopyranosido-1,6-mannitol and α-D-glucopyranosido-1,6-sorbitol by catalytic hydrogenation of α-D-glucopyranosido-1,6-fructose in aqueous solution with hydrogen at elevated pressure and elevated temperature, characterized in that the hydrogenation is carried out continuously at a hydrogen pressure of 100 to 400 bar, preferably 150 to 300 bar, and temperatures of 40° to 80° C., preferably 55° to 70° C., in the fixed-bed process in a reaction zone over support-free shaped bodies serving as hydrogenation catalysts and having a compressive strength of 20 to 250N, preferably 110 to 220N, and an internal surface area of 10 to 80 m²/g of (i) one or more elements of the iron sub group of sub group VIII which are additionally alloyed with (ii) elements of sub group VI having activating activity.

The compressive strength of the support-free shaped bodies can be determined in accordance with DIN 50 106.

The testing of support-free shaped bodies for the internal surface areas in accordance with the claims and thus for useability for the process according to the invention can be carried out by methods which have been described by F. M. Nelsen and F. T. Eggertsen, Analyt. Chem. 30 (1958), 1387 and S. J. Gregg and S. W. Sing, Adsorption, Surface Area and Porosity, London 1967, Chapters 2 and 8.

The iron sub group of sub group VIII of the Periodic Table of the Elements contains the elements iron, cobalt and nickel. The support-free shaped bodies to be used according to the invention contain one or more of these metals in amounts of at least 60, preferably at least 70, in particular at least 80% by weight, based on support-free shaped bodies.

Sub group VI of the Periodic Table of the Elements contains the elements chromium, molybdenum and tungsten. The support-free shaped bodies to be used according to the invention contain one or more of these metals in amounts of at least 0.1, preferably at least 0.3, in particular at least 0.5% by weight, based on support-free shaped bodies; they contain one or more of these metals in amounts of at most 20, preferably at most 10 and in particular at most 5% by weight, based on support-free shaped bodies.

The support-free shaped bodies to be used according to the invention can additionally contain—in each case based on support-free shaped bodies—up to 20, preferably up to 15, in particular up to 10% by weight of other metals; examples of such metals which do not have to be catalytically active include aluminium, silicon, titanium and manganese. According to a preferred embodiment the support-free shaped bodies, apart from components (i) and (ii) contain no more than 10% by weight of aluminium and no more than 5% by weight of other metals.

The process according to the invention permits the preparation of the crystallized mixture of both the diastereomeric sugar alcohols in a purity of over 99% in dry matter. The content of unreacted α-D-glucopyranosido-1,6-fructose reaches values of 0.2% by weight or below and the sum of sorbitol and mannitol is below 0.3% by weight.

Crystalline α-D-glucopyranosido-1,6-fructose can be used as starting compound for the process according to the invention α-D-Glucopyranosido-1,6-fructose can be prepared from sucrose solutions by enzymatic conversion with living or immobilized cell systems by known methods, (e.g. German Patent Specification 1 049 800). The starting material is preferably dissolved in oxygen-free deionized water.

According to a preferred embodiment, the following procedure is followed:

A 15 to 60% by weight strength, preferably 45 to 55% by weight strength, aqueous solution is prepared from αD-glucopyranosido-1,6-fructose and deionized drinking water, the pH of which aqueous solution is adjusted to 3.5–10.5, preferably 5–6.5. Crystalline α-D-glucopyranosido-1,6-fructose dissolved in water having a pH of 7 shows either a neutral reaction or—as a result of a trace formation of gluconic acid possibly caused by the Cannizarro reaction—shows a weakly acidic reaction. The desired pH adjustment can be made, e.g. by addition of an organic acid of the highest possible purity, such as citric acid, sorbic acid or sugar acids.

For the hydrogenation process, pure hydrogenation precompressed to a pressure of 100 to 400 bar, preferably 200 to 300 bar, is used. The hydrogenation is carried out continuously in the fixed-bed process on the metallic-type support-free shaped bodies serving as hydrogenation catalysts, either by allowing the solution to be hydrogenated to flow over the shaped bodies packed into a hydrogenation reactor arriving from below or above cocurrently with the previously admixed hydrogen or else arriving from below in the opposite direction to the hydrogen flowing in from above or vice versa (counter-current process).

The hydrogenation reactor can be either a single high-pressure tube made of steel or a steel alloy which is wholly or partly filled with the support-free shaped body, where at certain tube cross-sections, the employment of the support-free shaped body on hurdles (wire baskets or the like) can also be useful, or else an enclosed high-pressure tube bundle, the individual tubes of which are wholly or partly filled with support-free shaped bodies. Furthermore, instead of a relatively large individual reactors one after tubular reactor, an arrangement of a plurality of small individual reactors one after the other in a cascade can be operated.

The support-free shaped bodies can be produced by conventional methods by pressing the metal powder on tableting or pelleting machines at high pressure, where to improve the adhesive strength of the metal particles, graphite can also be used in amounts of 0.5 to 1.5%, by weight, based on the total weight of the constituents forming the catalyst, or adhesives can be used in small amounts. The support-free shaped bodies are preferably produced in an oxygen-free atmosphere in order to avoid surface oxidations. Tableted or pelletized shaped bodies having diameters from 3 to 7 mm are the most effective and the most expedient for the reaction conditions. The compressive strength of the shaped bodies is of considerable importance and according to the invention has values of 20 to 250N, preferably 110 to 220N. Lower compressive strengths lead to disintegration of the shaped body or to erosive wear which would produce a metallic contamination of the reaction product. The internal surface area of the shaped bodies is further of considerable importance and according to the invention has values of 10 to 80 $m^2/g$ and is decisive for as quantitative as possible conversion of the starting materials.

The hydrogenation process is carried out at a temperature of 40° to 80° C., preferably 55° to 70° C. Lower temperatures necessitate longer residence times or dispensing with a quantitative conversion of the α-D-glucopyranosido-1,6-fructose. Higher temperatures lead to increased formation of sugar alcohols of monosaccharids (sorbitol or mannitol) and to uncontrolled side reactions (caramelization, ether cleavage or hydrogenating cracking), which can lead to discolorations and the formation of further undesirable by-products.

The hourly catalyst productivity can be 45 to 60 g, preferably 50 to 55 g of α-D-glucopyranosido-1,6-fructose, mentioned as starting compound per liter of catalyst. When the reaction conditions mentioned are complied with, unexpectedly high catalyst service lives of 15,000 hours and above may be achieved, specific catalyst consumptions of 0.12% by weight or less being attained. The technical advantages of the process according to the invention, in addition to the high yield caused by the virtually quantitative conversion and the ecological advantages resulting from the purity of the prepared product, are therefore the extremely low catalyst consumption and the low catalyst costs.

The hydrogenated aqueous solution leaving the reactor which solution comprises the sugar alcohols α-D-glucopyranosido-1,6-mannitol and α-D-glucopyranosido-1,6-sorbitol in a ratio of 1:1 can, after depressurization in which the excess hydrogen can be collected and reused after repeated compression and make up with further hydrogen, and after filtration already be used as a sugar substitute in liquid form.

The water of this solution can be removed in various ways, for example via spraydriers, roller-driers or by freezedrying. It has proved to be expedient to concentrate the generally glass-clear sugar alcohol solution obtained to a sugar alcohol content of about 80% by weight in a falling-film evaporator or a similarly operating apparatus and then to bring the solution to complete crystallization after further evaporation in a vacuum crystallization apparatus. The crystals can be brought to a uniform grain size by a downstream grinding process and possibly screening.

Although the mixture of α-D-glucopyranosido-1,6-mannitol and α-D-glucopyranosido-1,6-sorbitol, which is formed in the hydrogenation of α-D-glucopyranosido-1,6-fructose, is flowable and appears to be completely dry, it has a water of crystallization content of approximately 5% by weight which is due to the fact that α-D-glucopyranosido-1,6-mannitol, in contrast to α-D-glucopyranosido-1,6-sorbitol, crystallizes with a water of crystallization content of about 10% by weight.

The product obtained begins to melt at 90° C. A clear melt forms at 140° C. The exact melting range of the anhydrous mixture of substances is obtained if, e,g., the anhydrous product is melted in an evacuable drying apparatus at 110° C. and 10 mbar and the water is allowed to evaporate quantitatively from the melt. A recrystallized sample thus treated shows a melting range of 138° to 143° C.

Both sugar alcohols which can be prepared according to the invention are known. They are used as individual substances and as a mixture, because of their pleasant sweet taste which in contrast to some other sugar alcohols is free of off-taste or accompanying taste, as low-calorie sugar substitutes which are also suitable for diabetics and are less cariogenic than sucrose.

In its solution behavior in water, the mixture of α-D-glucopyranosido-1,6-mannitol and α-D-glucopyranosido-1,6-sorbitol lies in the temperature range of 0°–70° C. between that of the pure substances. At temperatures above 70° C., the solubility of the mixture exceeds that of the pure substances which makes the use of the mixture as a sweetener for beverages and foods appear particularly advantageous whenever the substances in question have to be sweetened more intensively. Not only the individual compounds but also the mixture show a sweetening power which corresponds to about 45% of the sweetening power of sucrose. To increase the sweetening power of the mixture of α-D-glucopyranosido-1,6-mannitol and α-D-glucopyranosido-1,6-sorbitol, artificial sweeteners, e.g. cyclohexylsulphamate or aspartylphenylalanine methylester, can be added to the aqueous solution and the mixture can be obtained in crystalline form by joint vacuum crystallization. However, the artificial sweeteners can also be mixed in solid form with crystals. The mixture of α-D-glucopyranosido-1,6-mannitol and α-D-glucopyranosido-1,6-sorbitol can also be mixed in liquid or solid form with other sweet-tasting sugar alcohols, e.g. sorbitol, xylitol, mannitol and lactitol. Because of its high caramelization temperature, the mixture is particularly highly suitable as a sweet-tasting, structure-forming and body-forming filler for chocolate, filled chocolates and bakery products.

The percentages of the following examples are each by weight.

EXAMPLES

Example 1

A vertically upright, heat-insulated high-pressure tube made of stainless steel of 45 mm internal diameter and 1 m in length is packed with 1.4 1 of a hydrogenation catalyst prepared by tableting powder of an Ni/Mo alloy having an Mo content of 1.75%, which hydrogenation catalyst, at a cylinder height of 5 mm and a diameter of 5 mm, has a compressive strength of 191N and an internal surface area of 58 m²/g. Through this tube are continuously pumped 140 ml per hour of a 50% strength solution of α-D-glucopyranosido-1,6-fructose in deionized drinking water, which was adjusted to a pH of 6.0, together with the threefold molar amount of highly pure hydrogen at a pressure of 300 bar, more precisely rising from bottom to top.

Aqueous solution and hydrogen are conducted through a heat exchanger and heated to the extent that they enter the high-pressure tube at a temperature of 60° C. The mixture of aqueous solution and excess hydrogen leaving the high-pressure tube is conducted via a cooler into a separator, from where the hydrogen, after replacement of the amount used, is pumped back into the preheater together with non-hydrogenated solution and from there again into the high-pressure tube.

The clear aqueous solution is depressurized, filtered through a fine filter, concentrated in a falling-film evaporator to a sugar alcohol content of approximately 80% and then brought to complete crystallization in a vacuum crystallizer. The fine crystal powder obtained is composed of a mixture of α-D-glucopyranosido-1,6-mannitol and α-D-glucopyranosido-1,6-sorbitol in the ratio 1:1 in dry matter. The water content is 5%. The mixture of the two stereoisomeric sugar alcohols is otherwise highly pure (purity ≦99.1%). The content of non-hydrogenated α-D-glucopyranosido-1,6-fructose is ≦0.2%. The content of sorbitol is ≦0.2%. Mannitol could not be detected. After a running time of 3200 hours, the activity of the catalyst was unchanged.

Example 2

Through a high-pressure tube as in Example 1, but made of high-pressure steel N 9, an equal amount per hour of a 50% strength aqueous solution of α-D-glucopyranosido-1,6-fructose which has a pH of 5.5 is hydrogenated in reverse reaction flow to that described in Example 1 at a temperature of 65° C. and a hydrogen pressure of 200 bar. The catalyst was prepared by tableting powder of an Ni/Mo alloy having an Mo content of 1.62% and an Al content of 6.1%. The tablets, at a cylinder height of 5 mm and a diameter of 5 mm, have a compressive strength of 210N and an internal surface area of 71 m²/g.

After a running time of 1200 hours with undiminished activity, the content of α-D-glucopyranosido-1,6-mannitol and α-D-glucopyranosido-1,6-sorbitol of the reaction mixture evaporated to dryness in the rotary evaporator is 99.1%. The content of non-hydrogenated α-D-glucopyranosido-1,6-fructose is 0.2%. The content of sorbitol is 0.2%. The content of mannitol is 0.03%.

Example 3

In a high-pressure tube as in Example 1, an equal amount per hour of a 55% strength aqueous solution of α-D-glucopyranosido-1,6-fructose which has a pH of 6.5 is hydrogenated in the same manner as in Example 1 at a temperature of 55° C. and a hydrogen pressure of 300 bar. The catalyst was obtained by tableting a pulverized Ni/Fe/Mo alloy. The alloy has an Fe content in Ni of 15% and an Mo content of 1.4%. The tablets, at a cylinder height of 3 mm and a diameter of 3 mm, have a compressive strength of 162N and a surface area of 68 m²/g. The 1:1 mixture obtained in a vacuum crystallizer of α-D-glucopyranosido-1,6-mannitol and α-D-glucopyranosido-1,6-sorbitol has a purity of ≧99.1%. The content of unconverted α-D-glucopyranosido-1,6-fructose is 0.1%. The sorbitol content is 0.2%. The mannitol content is 0.08%. After a running time of 1100 hours, the activity of the catalyst was unchanged.

Example 4

In a high-pressure tube as in Example 1, the same amount of a 45% strength aqueous solution of α-D-glucopyranosido-1,6-fructose which has a pH of 5.5 is hydrogenated in the same manner as in Example 1 at a temperature of 65° C. and a hydrogen pressure of 200 bar. The catalyst was obtained by tableting a pulverized Ni/Mo alloy having an Mo content of 0.55%. The tablets, at a cylinder height of 5 mm and a diameter of 5 mm, have a compressive strength of 147N and an internal surface area of 44 $m^2/g$. The mixture obtained in a vacuum rotary tube of α-D-glucopyranosido-1,6-mannitol and α-D-glucopyranosido-1,6-sorbitol has a purity of 99.4%. The content of unconverted α-D-glucopyranosido-6-fructose is 0.2%. The sorbitol content is 0.25%. No mannitol can be detected. After a running time of 900 hours, the activity of the catalyst was still undiminished.

Example 5

In a high-pressure tube as in Example 1, an equal amount per hour of a 45% strength aqueous solution of α-D-glucopyranosido-1,6-fructose which has a pH of 6.5 is hydrogenated in the same manner as in Example 1 at a temperature of 70° C. and a hydrogen pressure of 300 bar. The catalyst was obtained by tableting a pulverized Ni/Mo/Al/Si alloy having an Mo content of 0.35%, an Al content of 5.4% and an Si content of 0.4%. The tablets, at a cylinder height of 5 mm and a diameter of 5 mm, have a compressive strength of 148N and an internal surface area of 61 $m^2/g$. The 1:1 mixture obtained in a vacuum crystallizer of α-D-glucopyranosido-1,6-mannitol and α-D-glucopyranosido-1,6-sorbitol has a purity of 99.1%. The content of unconverted α-D-glucopyranosido-1,6-fructose is 0.2%. The sorbitol content is 0.24%. The mannitol content is 0.05%. After a running time of 1600 hours, the activity of the catalyst was still unchanged.

Example 6

In a high-pressure tube as in Example 1, the same amount of a 45% strength aqueous solution of α-D-glucopyranosido-1,6-fructose which has a pH of 5.5 is hydrogenated in the same manner as in Example 1 at a temperature of 75° C. and a hydrogen pressure of 150 bar. The catalyst was obtained by tableting a pulverized Ni/Cr alloy which also contains Al. The alloy has a Cr content of 4.1% and an Al content of 5.4%. The tablets, at a cylinder height of 5 mm and a diameter of 5 mm, have compressive strength of 158N and an internal surface area of 58 $m^2/g$. The mixture obtained in a vacuum rotary tube of α-D-glucopyranosido-1,6-mannitol and α-D-glucopyranosido-1,6-sorbitol has a purity of 99.2%. The content of unconverted α-D-glucopyranosido-1,6-fructose is 0.2%. The sorbitol content is 0.15%. Mannitol can not be detected. After a running time of 1100 hours, the activity of the catalyst was still undiminished.

I claim:

1. A process for the preparation of mixtures of α-D-glucopyranosido-1,6-mannitol and α-D-glucopyranosido-1,6-sorbitol by catalytic hydrogenation of α-D-glucopyranosido-1,6-fructose in aqueous solution with hydrogen at elevated pressure and elevated temperature, characterized in that the hydrogenation is carried out continuously at a hydrogen pressure of 100 to 400 bar, and temperatures of 40° to 80° C., in the fixed-bed process in a reaction zone over support-free shaped bodies serving as hydrogenation catalysts having a compressive strength of 20 to 250N, and an internal surface area of 10 to 80 $m^2/g$ and comprising an alloy of at least three-metals, at least one of which is selected from the group consisting of iron, cobalt and nickel and at least one of which is selected from the group consisting of chromium, molybdenum and tungsten.

2. The process according to claim 1, characterized in that the shaped bodies are those composed of pressed metal powders.

3. The process according to claim 1, characterized in that the shaped bodies viewed macroscopically have a smooth surface.

4. The process according to claim 1, characterized in that the shaped bodies are cylindrical or spherical and have diameters from 3 to 7 mm.

5. The process according to claim 1, characterized in that the hydrogenation of the sugars is carried out in 15 to 60% aqueous solution at a pH of 3.5 to 8.5.

6. The process according to claim 1, characterized in that the catalyst comprises an alloy of nickel, molybdenum and aluminum.

7. The process of claim 1, wherein said alloy comprises, in addition to said at least one-metal selected from the group consisting of iron, cobalt and nickel, and said at least one-metal selected from the group consisting of chromium, molybdenum and tungsten; one or more metals selected from the group consisting of aluminum, silicon, titanium and manganese, wherein the amount of aluminum, if present, is not more than 10% by weight of alloy and the amount of silicon, titanium or manganese, if present, is not more than 5% by weight of alloy.

8. The process of claim 7, wherein said alloy is an alloy of nickel, iron and molybdenum.

9. The process of claim 7, wherein said alloy is an alloy of nickel, molybdenum, aluminum and silicon.

10. The process of claim 7, wherein said alloy an alloy of nickel, chromium and manganese.

11. The process of claim 7, wherein said alloy is an alloy of nickel, chromium and titanium.

12. The process of claim 7, wherein said alloy is an alloy of nickel, iron and chromium.

* * * * *

UNITED STATES PATENT AND TRADEMARK OFFICE
CERTIFICATE OF CORRECTION

PATENT NO. : 5,644,044
DATED : July 1, 1997
INVENTOR(S) : Gerhard Darsow

It is certified that error appears in the above-identified patent and that said Letters Patent is hereby corrected as shown below:

Col. 8, Line 51              After "said alloy" insert --is--

Title Page, U.S. Documents   Insert --   4,233,439, 11/1980, Schiweck, et al. 536/4--
                             5,253,993  10/1993, Birkenstuck, et al. 425/78 --

Title Page, Foreign Patent   Insert --0152779  8/1985, Europe
Documents                            554074    6/1932  Germany
                                     4026351   2/1992  Germany
                                     0423525   4/1992  Europe
                                     2520173  12/1976, Germany--

Signed and Sealed this

Nineteenth Day of October, 1999

Attest:

Attesting Officer

Q. TODD DICKINSON

Acting Commissioner of Patents and Trademarks